United States Patent [19]

Crosby et al.

[11] 4,036,869
[45] July 19, 1977

[54] 2,4-DIISOCYANATO BICYCLO (3,3,0)-OCT-6-ENE

[75] Inventors: John Crosby; Robert Allan Campbell Rennie, both of Runcorn, England; Robert Michael Paton, Edinburgh, Scotland

[73] Assignee: Imperial Chemical Industries Limited, London, England

[21] Appl. No.: 740,244

[22] Filed: Nov. 8, 1976

Related U.S. Application Data

[62] Division of Ser. No. 638,655, Dec. 8, 1975.

[30] Foreign Application Priority Data

Dec. 11, 1974   United Kingdom ............... 53551/74

[51] Int. Cl.² ......................................... C07C 119/045
[52] U.S. Cl. .............................................. 260/453 AP
[58] Field of Search ................................. 260/453 AP

[56] References Cited

U.S. PATENT DOCUMENTS 3,222,387  12/1965  Brachel et al. ............... 260/453 AP

*Primary Examiner*—Dolph H. Torrence
*Attorney, Agent, or Firm*—Cushman, Darby & Cushman

[57] ABSTRACT

2,4-diisocyanato bicyclo (3,3,0)-oct-6-ene, a new compound and its preparation and use are disclosed.

1 Claim, No Drawings

2,4-DIISOCYANATO BICYCLO (3,3,0)-OCT-6-ENE

This is a division of application Ser. No. 638,655 filed Dec. 8, 1975.

This invention relates to the production of isocyanates and, especially, to the production of aliphatic polyfunctional isocyanates, that is, compounds containing two or more isocyanate groups in the molecule, by thermal decomposition of furoxans.

A process for the production of isocyanates by the thermal decomposition of furoxans is described and claimed in our copending British Pat. No. 34203/72 (German equivalent published as OLS No. 2,336,403). It is thought that, in this process, the furoxan ring opens to give a mono- or dinitrile oxide which then rearranges to form the corresponding isocyanate. However, when this process is applied to furoxans in which the carbon atoms of the furoxan ring form part of a strained aliphatic ring system it is difficult to control the rearrangement of nitrile oxide to isocyanate with the result that, in some cases, isocyanate can not be obtained from the reaction mixture.

We have now found that if the reaction is made to proceed in the presence of sulphur dioxide the reaction is much more readily controllable, especially when the furoxan has the aforementioned strained ring structure, and gives rise to isocyanate substantially free from by-products.

According to the present invention, a process for the production of an organic isocyanate comprises heating a furoxan in the presence of sulphur dioxide to give an isocyanate.

Suitable furoxan starting materials include those of general formula

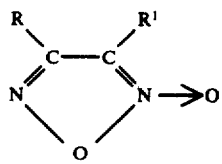

where R and R¹, which may be the same or different, are either separate hydrocarbon groups which may be aliphatic or aromatic containing from 1 to 18 carbon atoms or, alternatively, may form part of a second ring system fused to the furoxan ring. This second ring may itself form part of a multiple ring system which is preferably aliphatic, such as the norbornane structure.

The process of the present invention is most useful when applied to furoxans in which R and R¹ form a second ring system at least that part of it which incorporates the carbon atoms of the furoxan ring being a strained aliphatic ring containing not more than 5 carbon atoms. Such furoxans commonly ring-open at temperatures below 180° C or even 100° C and it is when our process is applied to such furoxans that its benefits are most marked.

Examples of such furoxans include (a) "dicyclopentadiene" furoxan, (b) 3,4 propano furoxan, and (c) "camphor" furoxan,

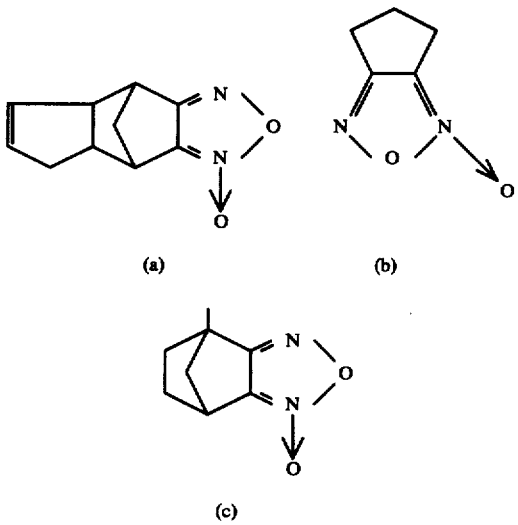

and furoxans having the following structural formulae:

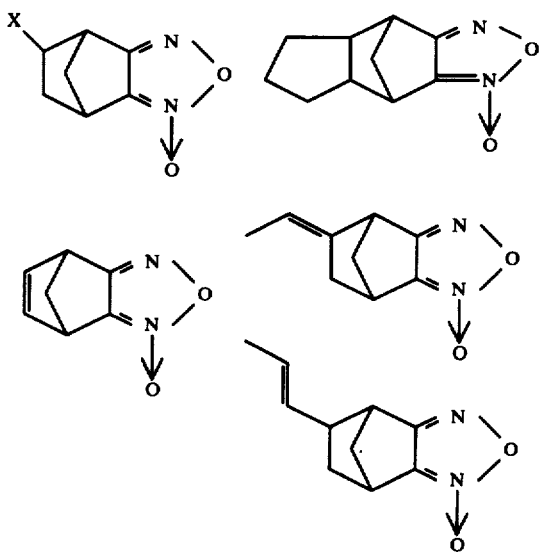

where X represents for example a hydrogen, alkyl, alkyl carboxy or nitrile group. When R and R¹ are separate groups, mono-isocyanates are formed; but when they form part of a ring the products are diisocyanates.

The temperature to which the furoxan is heated in our process will depend upon its composition and also the length of time for which it is to be heated. However, temperatures will usually fall within the range 0° to 300° C and preferably between 60° and 180° C.

The sulphur dioxide may be in the gaseous or liquid form. When the sulphur dioxide is used in liquid form it may constitute the only liquid component of the reaction mixture; but the furoxan is preferably dissolved in an inert solvent and gaseous sulphur dioxide dissolved in the solvent so that sulphur dioxide is always present during the reaction. Conveniently the solvent is saturated with sulphur dioxide gas at a temperature lower than that at which the reaction is to be carried out so that the presence of sulphur dioxide is readily maintained during the reaction. However, it may be desirable to maintain the reactants at super-atmospheric pressure to prevent undue loss of sulphur dioxide, and/or to pass sulphur dioxide gas into the reactants during reaction.

One convenient way of carrying out the process of our invention is to feed furoxan solution continuously to a reaction vessel containing a sulphur dioxide-containing medium, which is initially heated to reaction temperature.

It will be appreciated that the process lends itself to either a batchwise or continuous mode of operation.

Suitable solvents, which include hydrocarbons, halogenated hydrocarbons, or ethers, should be inert to the reactants and products and have boiling points (under super-atmospheric pressure, if necessary) sufficiently high to enable the furoxan to be maintained at the appropriate temperature. Examples of preferred solvents include toluene, xylene and dimethylformamide. Preferably the solvent is chosen so that the reaction may be carried out at its reflux temperature.

It is convenient to choose a solvent with a b.pt. sufficiently different from that of the product isocyanate to allow separation by simple distillation.

The concentration of furoxan dissolved in the solvent may be varied over a considerable range, depending on its solubility, but in general concentrations in the range 2 to 10% by weight are convenient.

In general, the products of our process are clean and substantially free of by-products, especially chlorine-containing by-products which commonly occur in the production of isocyanate using conventional routes. Furthermore, separation of the product from our reaction mixtures is usually very simple, as the sulphur dioxide and solvent may be removed by distillation. It is often convenient to conduct such distillations under reduced pressure and, hence, at reduced temperature to minimise the likelihood of thermal degradation of the isocyanate product.

By using the process of our invention it is possible to simplify preparation of many isocyanates and, in some cases, to prepare isocyanates which are difficult if not impossible to prepare by other methods.

For example, if dicyclopentadiene furoxan (DCPDF) is refluxed in a suitable inert solvent in the absence of sulphur dioxide no isocyanate is isolated. However, when DCPDF is subjected to thermal decomposition in accordance with our present process 2,4-diisocyanato bicyclo (3,3,0)-oct-6-ene is produced in high yield with substantially no by-product.

We thus provide 2,4,-diisocyanato bicyclo (3,3,0)-oct-6-ene as a novel compound.

3,4-Propano furoxan also failed to give an isocyanate when refluxed in an inert solvent in the absence of sulphur dioxide, whereas in its presence it gave rise to 1,3-diisocyanato propane.

Furoxans for use as starting materials in the process of our invention may be made by any suitable route; but it may be convenient to prepare them by the addition of dinitrogen trioxide to a cyclic olefin to form the pseudonitrosite which can then be isomerised to the nitrooxime which may be cyclised with loss of water to give the furoxan. This latter method is described and claimed in our aforementioned copending British Pat. No. 34203/72, and German published OLS No. 2,336,403, the disclosure of which is incorporated herein by reference. Alternatively the furoxans may be prepared from the appropriate cyclic alkanone by the method of Ackrell et al. (J C S Perkin I, (1972), p. 1587).

Isocyanates prepared by the process of our invention may be used to form urethanes by reaction with suitable hydroxylic compounds. For example they may be reacted with bifunctional and/or trifunctional polyalkylene glycols or with other hydroxyl-ended polymers such as polyethylene tetramethylene adipate, to form polyurethanes. The reaction between isocyanate and hydroxylic compound may be readily carried out using known techniques for the manufacture of polyurethanes, in the presence of a suitable catalyst, for example dibutyl tin dilaurate. Similarly they may be reacted with suitable amino compounds to form ureas and with other materials commonly reacted with isocyanates.

The invention will be illustrated by the following Examples.

It will be appreciated that many of the products referred to in the Examples may exist in more than one isomeric form.

Preparation of Dicyclopentadiene Furoxan (DCPDF)

Step A:
Synthesis of dicyclopentadiene pseudonitrosite

A well stirred solution of dicyclopentadiene (66g) in n-pentane (1 liter), cooled in an ice bath, was treated with a mixed stream of nitric oxide (150 ml/min) and air (75-100 ml/min) for 3 hours. The mixture was purged with nitrogen and the solid product filtered off, sucked dry, washed with hot methanol and dried to give an almost colourless crystalline material, wt. 69g (66%) mp 122°-140° C, infra-red spectrum (Nujol mull) strong band at 1555 cm$^{-1}$.

Step B:
Synthesis of nitro oxime

The nitroso dimer from the previous preparation (20g) was heated at reflux under nitrogen in dioxan (500 ml) until the initial green colouration disappeared (40 minutes). Removal of the solvent afforded a yellow oil which slowly crystallised. Washing with methanol gave 7.5 g of clean crystalline material with mp 135°-150° C.

Step C:
Synthesis of dicyclopentadiene furoxan

The nitro oxime from the previous preparation (2.20 g) and 2.3 g of a standardised DMF-SO$_3$ mixture (containing 5% excess SO$_3$ over the stoichiometric amount required for the dehydration reaction) were mixed; a further 1.5 ml of DMF was added to ensure the mixture was completely liquid at room temperature. The mixture was then set aside at room temperature in a stoppered flask for 65 hours.

The mixture was poured into water (60 ml) and extracted with dichloromethane (2 × 30 ml) to remove DMF. The acidic aqueous layer was then treated with 1N aq. NaOH until the pH was approximately 8.5. The resulting emulsion of furoxan was extracted with CH$_2$Cl$_2$ (3 × 20 ml); the extracts were dried and evaporated to give crude furoxan as a pale yellow oil which crystallised on standing to give the crude product (2.05 g).

Crystallisation from ether-heptane afforded the pure furoxan as pale yellow crystals:
Yield 1.31 g = 62%
mp 98°-100° C
I.R. 1655 cm$^{-1}$ (very strong) characteristic of furoxans
C$_{10}$H$_{10}$H$_2$O$_2$ requires: 63.1%C, 5.26%H, 14.7%N.
found: 63.1%C, 5.67%H, 14.6%N.

NB DCPDF may be handled safely in solution. However, when heated to 80°-85° C on a gram scale, the solid decomposes explosively.

Preparation of 2,4-Diisocyanato Bicyclo (3,3,0)-Oct-6-ene (DIBCOE)

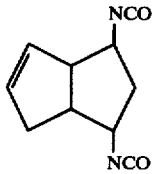

EXAMPLE 1

Dry toluene (50 ml) was saturated with $SO_2$ gas and DCPDF (2.0 g) was added. The solution was heated at reflux for 30 minutes under $N_2$ and allowed to cool. The solution was evaporated at 35° C under reduced pressure to give the crude isocyanate (1.8 g, 90% yield). Distillation of the crude isocyanate (DIBCOE) under reduced pressure afforded purified isocyanate (78% yield) as a colourless oil.

Infra red spectrum: 2260 cm$^{-1}$ (very strong).

'Hnmr: τ8.3 (1H); 7.8 (1H); 7.4 (2H); 7.2 (1H); 6.6 (1H); 6–6.2 (2H); 4.4 (1H); 4.1 (1H).

Analysis: $C_{10}H_{10}N_2O_2$ requires: 63.1%C; 5.26%H; 14.7%N. found: 62.8%C; 5.44%H; 14.8%N.

EXAMPLE 2

DCPDF (2.0 g) was dissolved in dimethylformamide (50 ml) which had been saturated with $SO_2$. After heating under nitrogen for 30 min at 130°-140° C the solution was examined by infra red spectroscopy and shown to contain the isocyanate.

EXAMPLE 3

DCPDF (2.0 g) was added to orthodichlorobenzene (50 ml) saturated with gaseous $SO_2$ and allowed to stand at room temperature for 3 days. Spectroscopic examination of the solution showed no sign of isocyanate but when the solution was then heated to 150° C for 30 minutes under $N_2$ isocyanate was produced.

Characterisation of 2,4-Diisocyanato Bicyclo (3,3,0)-Oct-6-Ene as the Bis-Methyl Urethane

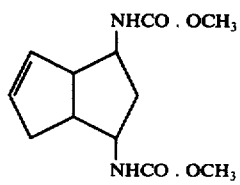

The diisocyanate (2.0 g) produced as described under Example 1 and excess methyl alcohol were mixed; two drops of triethylamine were added as catalyst and the solution was left for 24 hours at room temperature. Evaporation of the excess solvent followed by washing of the residual crystalline product with diethylether afforded the bis-methyl urethane as colourless crystals: (2.4 g, 89% yield), Mpt 185°-188° C. Infra red: 1690 cm$^{-1}$ (C=O).

Analysis: $C_{12}H_{18}N_2O_4$ requires: 56.7%C; 7.09%H, 11.0%N. found: 57.4%C; 7.31%H; 11.0%N.

Characterisation of 2,4-Diisocyanato Bicyclo (3,3,0)-Oct-6-Ene as the Bis-Phenyl Urea

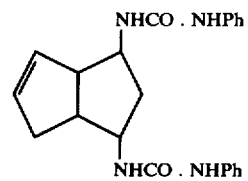

The diisocyanate (2.0 g) produced as described under Example 1 and excess aniline were mixed and the solution left for 15 hours at room temperature. A white precipitate of the urea separated out and was filtered off (4.1 g, 100% yield). Infra red: 1640 cm$^{-1}$(C=O), 1600, 1545 (Ph)

Analysis: $C_{22}H_{24}N_4O_2$ requires: 70.2%C; 6.39%H, 14.9%N. found: 69.02%C; 6.33%H; 14.8%N.

'Hnmr: τ1.6 (1H); 2.5-3.2 (10H); 3.5 (1H); 4.05 (1H); 4.43 (1H); 6.0 (2H); 6.7 (3H); 7.1 (1H); 7.7 (2H); 8.1 (2H).

Preparation of Cross-Linked Polyurethanes Using DIBCOE

EXAMPLE 4

A mixture was prepared containing a bifunctional polypropylene glycol of hydroxyl value 56, m wt. 2000, a trifunctional polypropylene glycol of hydroxyl value 56 m wt. 3000 and DIBCOE, the molar ratio of the three components being 3:1:1.07. One drop of dibutyl tin dilaurate catalyst was added to the mixture which was cured at 125° C for 4 hours to give a clear, colourless rubbery product.

EXAMPLE 5

Polyethylene tetramethylene adipate (m wt. 1915) (1.0 mole), 1,4 butane diol (1.50 mole), trimethylolpropane (0.33 mole) and a small amount of dibutyl tin dilaurate catalyst were mixed together, dried, and degassed under vacuum. DIBCOE (3.0 mole) was then added to the mixture which was again degassed and then cast at 70° C between glass plates, and cured at 100° C for 16 hours. The cross-linked polyurethane sheet which resulted had the following properties.

| | |
|---|---|
| Tensile strength | 210 kg cm$^{-2}$ |
| Hardness (IRHD) | 69 |
| Elongation at break | 600% |
| Modulus (100%) | 10 kg cm$^{-2}$ |
| Modulus (300%) | 18 kg cm$^{-2}$ |

EXAMPLE 6

Preparation of Thermoplastic Polyurethane

Polyethylene tetramethyleneadipate (13.7 g), 1,4 butane diol (1.76 g), DIBCOE (5 g) and dibutyl tin dilaurate were mixed and degassed as described under Example 5. The mixture was cast between glass plates at 70° C and cured at 100° C for 16 hours.

The product was a thermoplastic, clear, colourless sheet, which could be injection moulded. When a piece of the material was pressed at 120° C at 400 psi the moulded product had a tensile strength of 425 kg cm$^{-1}$.

EXAMPLE 7

Preparation of 1,3-Diisocyanatopropane 3,4-Propanofuroxan (0.88 g)

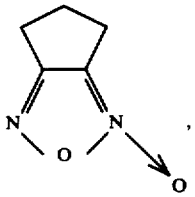

was added to an SO$_2$-saturated solution of dry xylene (20 ml). After 30 min at reflux under N$_2$ spectroscopic examination of the solution showed the presence of the diisocyanate.

EXAMPLE 8

Preparation of 1,3-Diisocyanato-1,2,2-Trimethylcyclopentane

"Camphor furoxan",

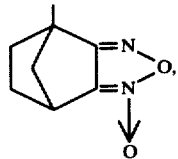

(1.1 g) was added to ortho-dichlorobenzene which had been saturated with dry SO$_2$ gas. After 2 hours at reflux under N$_2$ infra red examination of the solution showed strong absorption at 2250 cm $^{-1}$. The solution was evaporated to give a dark oil, this oil was subsequently decolourised with activated charcoal in toluene and evaporated to give the diisocyanate as a straw coloured oil (0.9 g, 82% yield).

The diisocyanate from Example 8 was characterised:
i. As the bis-methyl urethane

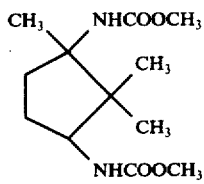

The diisocyanate was mixed with an excess of methyl alcohol, two drops of triethylamine were added to the mixture as a catalyst, and the mixture was left for 24 hours at room temperature. Excess methanol was evaporated and the residual crystalline product was washed with diethyl ether. The product bis-methyl urethane was in the form of colourless cyrstals, having a mpt of 134°–136° C.

Analysis C$_{12}$H$_{22}$N$_2$O$_4$ requires: 55.8%C; 8.53%H; 10.85%N. found: 55.7%C; 8.90%H; 11.01%N.

ii. As the bisphenyl urea

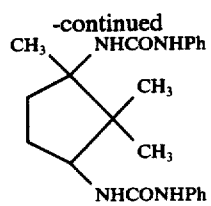

The diisocyanate was mixed with an excess of aniline and the mixture allowed to stand at room temperature for 15 hours. The white precipitate which formed was filtered off and shown to be the required bisphenyl urea.

Analysis: C$_{22}$H$_{28}$N$_4$O$_2$ requires: 69.4%C; 7.37%H; 14.7%N. found: 69.2%C; 7.33%H; 14.5%N.

EXAMPLE 9

Preparation of Isocyanate from Brominated DCPDF

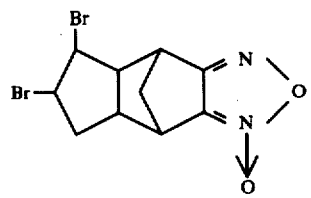

DCPDF was brominated by reaction with bromine in carbon tetrachloride at 0° C. The brominated compound (50 mg) was added to toluene which had been saturated with SO$_2$ gas. The mixture was refluxed for 10 minutes and then cooled. The presence of isocyanate was detected by infra red spectroscopy, which gave a strong absorption at 2270 cm $^{-1}$.

EXAMPLE 10

Preparation of 2,4 Diisocyanato-1-Methyl Cyclopentane

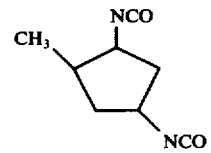

Methyl norbornene furoxan

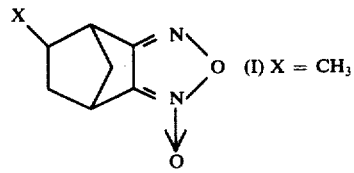

was prepared by the procedure described above for the preparation of DCPDF, except that 2-methyl 5 norbornene was used instead of dicyclopentadiene as starting material. The furoxan thus obtained was then subjected to the procedure of Example 1 to produce 2,4 diisocyanato-1-methylcyclopentane. The product gave an infra red absorption at 2260 cm $^{-1}$.

Analysis: C$_8$H$_{10}$N$_2$O$_2$ requires: 57.8%C; 6.03%H; 16.86%N. found: 58.6%C; 6.54%H; 16.65%N.

The product was characterised as the phenyl urea derivative, prepared as described under Example 3. The phenyl urea had a m.pt of 220°-224° C and I.R. absorption at 1640 cm$^{-1}$ (C=O).

Analysis: $C_{20}H_{24}N_4O_2$ requires: 68.8%C; 6.82%H; 15.92%N. found: 68.1%C; 6.93%H; 15.70%N.

EXAMPLE 11

Preparation of a Cross-linked Polyurethane

The diisocyanate product from Example 10 (3.0 mole), polyethylene tetramethylene adipate of m. wt. 1915 (1.0 mole), 1,4 butane diol (1.50 mole), trimethylolpropane (0.33 mole) and dibutyl tin dilaurate were mixed and degassed as described under Example 5. The mixture was then cured between glass plates at 100° C for 16 hours. A clear, colourless, soft rubbery sheet material was obtained, having the following properties.

| Hardness (IHRD) | 64 |
| --- | --- |
| Tensile strength | 160 kg cm$^{-2}$ |
| Elongation at break | 585% |
| Modulus (100%) | 13 kg cm$^{-2}$ |
| Modulus (300%) | 22 kg cm$^{-2}$ |

EXAMPLE 12

Preparation of 2,4 Diisocyanato-1-Cyanocyclopentane

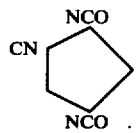

"Cyano norbornene" furoxan, (I) X=CN, was prepared by the procedure used for the preparation of DCPDF, with the exception that 2-cyano-5-norbornene was used instead of dicyclopentadiene as starting material. The furoxan thus obtained ws then subjected to the procedure of Example 1 to produce 2,4, diisocyanato-1-cyanopentane. The product was an oil having a b.pt. of 120°-130° C at 0.15 mm Hg pressure. The I.R. spectrum gave a strong absorption at 2260 cm$^{-1}$ (NCO)

Analysis: $C_8H_7N_3O_2$ requires: 54.25%C; 3.95%H; 23.75%N. found: 54.48%C; 3.84%H; 23.58%N.

The above procedure was repeated using dioxan as solvent instead of toluene, with similar results.

The diisocyanate product was characterised as the bis methyl urethane using the procedure given under Example 3.

Analysis $C_{10}H_{15}N_3O_4$ requires: 49.55%C; 6.22%H. found: 49.80%C; 6.26%H.

EXAMPLE 13

Preparation of 2,4-Diisocyanato-1-Acetoxy Cyclopentane

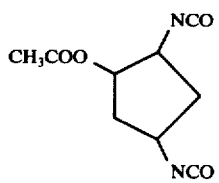

"Acetoxy norbornene" furoxan, (I) X=CH$_3$COO was prepared by the procedure used for the preparation of DCPDF, with the exception that 2-acetoxy-5-norbornene was used instead of dicyclopentadiene as starting material. The furoxan thus obtained was then subjected to the procedure of Example 1 to produce 2,4-diisocyanate-1-acetoxy cyclopentane. The infra red spectrum of the product had an absorption at 2260 cm$^{-1}$ (NCO).

EXAMPLE 14

Preparation of 2,4-Diisocyanatobicyclo (3,3,0) octane

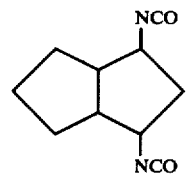

Bicyclo (3,3,0) octano (2,4) furoxan (0.53 g), prepared by the method of Ackrell et al. (*J C S Perkin I*, (1972) p. 1587) was added to dry toluene (100 ml) saturated with sulphur dioxide. The solution was heated at reflux under an atmosphere of nitrogen for 30 minutes, cooled, and the solvent removed under reduced pressure. The resulting crude diisocyanate was distilled to give pure material (55% yield, b. pt 90°-100° at 0.6 mm Hg). The infra red spectrum had an absorption at 2250 cm$^{-1}$ (very strong). 'Hnmr:τ8.3-8.6 (6H); 8.2 (1H); 7.8 (1H); 7.4 (2H); 6.6 (2H).

Characterisation as Bis-Phenyl Urea

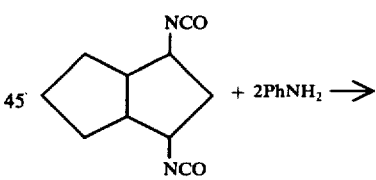

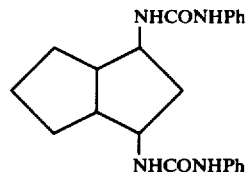

The crude diisocyanate produced as described above (0.50 g), was treated with a solution of aniline (0.50 g) in dry ether (10 ml) and set aside at room temperature for 16 hours. The solid product was filtered off and recrystallised from ethanol to give the bis-phenyl urea derivative as white needles (73% overall yield from the furoxan). M.pt. 258°-260° C

What we claim is:
1. 2,4-diisocyanato bicyclo (3,3,0)-oct-6-ene.

* * * * *